United States Patent [19]

Cohen

[11] Patent Number: 4,832,048

[45] Date of Patent: May 23, 1989

[54] SUCTION ABLATION CATHETER

[75] Inventor: Donald Cohen, Encino, Calif.

[73] Assignee: Cordis Corporation, Miami, Fla.

[21] Appl. No.: 113,985

[22] Filed: Oct. 29, 1987

[51] Int. Cl.$^4$ .............................................. A61N 1/00
[52] U.S. Cl. .................................. 128/786; 128/642; 128/303.13
[58] Field of Search ............... 128/752, 783, 784, 785, 128/786, 303.1, 303.13, 639, 642; 604/20, 313

[56] References Cited

U.S. PATENT DOCUMENTS

| | | | |
|---|---|---|---|
| 3,911,928 | 10/1975 | Lagergren | 128/786 |
| 4,347,842 | 9/1982 | Beale | 604/20 |
| 4,413,636 | 11/1983 | Jasso | 128/786 |
| 4,582,067 | 4/1986 | Silverstein et al. | 128/662.06 |
| 4,641,649 | 2/1987 | Walinsky et al. | 128/303.13 |
| 4,697,595 | 10/1987 | Breyer et al. | 128/662.06 |
| 4,719,914 | 1/1988 | Johnson | 128/303.1 |

OTHER PUBLICATIONS

Brochure-Cordis Corporation-Cordis Ducor Lumelec Electrode Catheters (2 pages), Dec., 1984.
Article entitled Cardiac Pacing-Electrophysiology, Tachyarrhythmias, by Polgar et al.,-Madrid, 1985, pp. 1582–1587.
Article entitled Comparison of Two Different Techniques for Closed-Chest His Bundle Ablation, by P. Polgar et al., pp. 1578 through 1581.
Article entitled Catheter Ablation in Dysrhythmias by Paul C. Gillette, M.D., Cardio, Mar. 1984 (pp. 67 through 69).
Article entitled Transvenous Catheter Ablation of a Posteroseptal Accessory Pathway in a Patient with the Wolff-Parkinson-White Syndrome by Fred Moraday, M.D. and Melvin M. Scheinman, M.D., Medical Intelligence (vol. 310, No. 11-pp. 705–707) (3/15/84).
Article entitled Closed-Chest Ablation of His Bundle: A New Technique Using Suction Electrode Catheter and DC Shock by P. Polgar et al.-Nachdruck aus: Cardiac Pacing pp. 883–890 (1983), Dr. D. Steinkopff Verlag Darmstadt.

Primary Examiner—Francis Jaworski
Assistant Examiner—George Manuel
Attorney, Agent, or Firm—Gerstman & Ellis, Ltd.

[57] ABSTRACT

A suction ablation catheter, for use in inactivating portions of the heart's conduction system to prevent abnormal heartbeat rates, comprises a tubular body having an open, distal end and a proximal aperture for applying suction through the catheter and through the distal end. The catheter also has an electrode at or adjacent the distal end, and an electrode lead extending along the catheter for communication by the electrode with a power source. In accordance with this invention, a tubular, insulating member made of refractory material is positioned adjacent the distal end, the electrode being positioned within the insulating member to localize the effects of electrical pulses emitted from the electrode.

16 Claims, 1 Drawing Sheet

SUCTION ABLATION CATHETER

BACKGROUND OF THE INVENTION

Certain abnormalities of either the cardiac muscle or the conductive system of the heart can result in pathologically high heart rates. If the high rate or tachycardia originates in the atrium, it is called a supraventricular tachycardia, which is transmitted to the ventricles, through the atrioventricular node (A-V node) and into the ventricular conduction system. Another source of an abnormal heart rate is a reentry path that is often located within the AV node.

In the two medical conditions cited above, as well as other causes of tachycardia, it is often mandatory to suppress the abnormally high rate. The treatment of choice is suppression by drug therapy. However, in certain instances, such therapy is not successful, and other avenues must be explored. Overdriven suppression in one method of treatment, where one applies cardiac stimulation at a rate above the tachycardia rate. As the abnormally high rate is controlled, the stimulation rate, applied by a cardiac pacer, is reduced to a normal level.

As a last resort, surgical intervention takes place in the form of a thoracotomy, which involves the mapping or location of the abnormal electrical activity, followed by the destruction of the appropriate structure. If the inner surfaces of the ventricles are to be mapped, then not only is a thoracotomy required, but also the patient must be placed on circulatory bypass, with its attendant risks.

It is desirable to achieve selective destruction or ablation of the appropriate structure using catheter techniques rather than major surgery. Various electrode configurations on a catheter have been suggested for use in such procedures. The catheter is introduced into the heart via an appropriate vein. Under fluoroscopic control, the electrodes carried on the catheter are positioned at various places on the heart wall and the detected electrical activity recorded. However, with many catheter designs no means have been available to destroy the site of abnormal activity located in this manner.

Mapping catheters have also been suggested, having an optical fiber which can transmit laser energy, or which carry a heating element, to destroy the pinpointed source of abnormal action.

Also, a catheter has been used which can deliver a powerful electric shock to an aberrant focus, thereby destroying it. In use, once the abnormal focus has been identified, suction may be applied, stabilizing an electrode-bearing catheter tip by drawing cardiac tissue into the lumen of a protruding tubular electrode. Then, the electric (typically D.C.) shock is applied, thereby destroying the focus.

The use of such a catheter has not been without its attendant difficulties. Because of the thinnes of the tubular electrode, coring of the tissue into the electrode has occurred during the process. If this occurs in the A-V node area, a septal defect may occur. Further, because the electrode delivers a D.C. shock, with its attendant high temperature, thermal destruction of both the electrode and the catheter material to which the electrode is bonded can occur. When such catheter damage occurs, foreign material may be left in the cardiovascular system. Also, to continue the process, the physician must then insert another catheter into the heart.

The suction/ablation catheter of this invention provides for the elimination of coring of cardiac tissue, as well as the prevention of electrode and catheter destruction by the heat generated during the electric shock. Thus it is safer to use, and it can be used repeatedly in the same patient, particularly for dealing with multiple sites in a heart causing tachycardia.

DESCRIPTION OF THE INVENTION

In accordance with this invention, a catheter is provided which may typically be used in mapping procedures, and is generally called a suction ablation catheter. The catheter comprises a tubular body having a bore, having an open distal end, and having a proximal aperture for applying suction through said catheter to the distal end.

The catheter also has an electrode at or adjacent the distal end, and an electrode lead extending along the catheter for communication of the electrode with a power source.

As the improvement of this invention, a tubular, refractory, insulating member is positioned adjacent the distal end, such insulating member often defining the distal end. The electrode is positioned within the tubular, insulating member. The effect of this is to localize the effects of electrical pulses emitted from the electrode.

Accordingly, the tubular catheter may be positioned at an appropriate place in the heart, so that the source of abnormal heart activity rests against the open, distal end of the catheter. The detection of this abnormal tissue may be accomplished by the electrode, used in a sensing mode, or alternatively a second sensing electrode carried on the catheter.

When the catheter has been properly oriented so that the abnormal heart tissue rests against the open, distal end of the catheter, suction may be applied through the proximal aperture to cause the abnormal heart tissue to be slightly drawn into the open, distal end of the catheter.

At this point, the electrode may be fed a strong electrical pulse, typically a direct current pulse having an energy on the order of 20 joules, sufficient to inactivate or destroy the tissue within and possibly adjacent the open, distal end of the catheter. However, the presence of the tubular, refractory, insulating member within which the electrode resides serves to localize the effects of such an electrical pulse to tissue which is in the immediate area of the open, distal end. Tissue located somewhat to the side of the refractory, insulating member may be untouched, having been protected by the refractory, insulating material.

Also, when the electrode used in this invention has a larger cross-sectional area, it is possible for there to be a lower peak current density (thereby limiting combustion) and a more uniform current distribution so that applied energy is more effective. This, in turn, can lower the energy required to accomplish the desired purpose.

Alternatively, alternating current for radio frequency (RF) cautery may be utilized rather than a direct current pulse. Thus, any voltage source, typically 0 to 1 GHz, may be used.

Accordingly, the intentional damage done to heart tissue may be localized, being of pinpoint rather than widespread action, to limit undesired damage to heart tissue, particularly since less energy can be used for the reasons described above.

The electrode used in the catheter of this invention may be of tubular shape, fitting inside the bore of the tubular, insulating member. Also, the insulating member is preferably made of a ceramic which is capable of withstanding and insulating against momentarily high electrode temperatures, thus providing its refractory characteristic. The heat generated by the electrode is only slowly transmitted through the insulating member to surrounding tissue, to avoid unintended burning of the tissue after the pulse has been emitted.

Preferably, the electrode may be made of an alloy which does not significantly degrade at a temperature of at least 2000 degrees C. and preferably about 3000 degrees C., for example appropriate, nontoxic alloys of tungsten, rhenium, titanium, or combinations thereof. Also, platinum and/or iridium alloys may be used.

The insulating member also serves to protect the material of the tubular catheter body, which may include silicone rubber, polyurethane, or the like as a casing material. Such materials may be shielded from the momentarily hot electrode by the insulating member, to avoid heat damage of the catheter body at the distal end thereof.

The catheter of this invention may have a tubular insulating member which comprises a first section of relatively small inner and outer diameters. The catheter may define a tubular main body into which the first section projects and is secured. The insulating member also comprises a second section of larger inner and outer diameters, the second section serving to define the distal catheter end. Also, the second section may carry the electrode, which may also be of tubular shape, with an aperture being generally positioned in the insulating member to permit the lead to communicate through it into contact with the electrode.

Alternatively, a tubular electrode may project into the tubular, main body of the catheter, being secured therein. A portion of the electrode also projects out of the main body of the catheter, with the tubular, insulating member surrounding that electrode portion and secured thereto by an appropriate adhesive, by mechanical means, or the like.

DESCRIPTION OF SPECIFIC EMBODIMENTS

Figure 1:
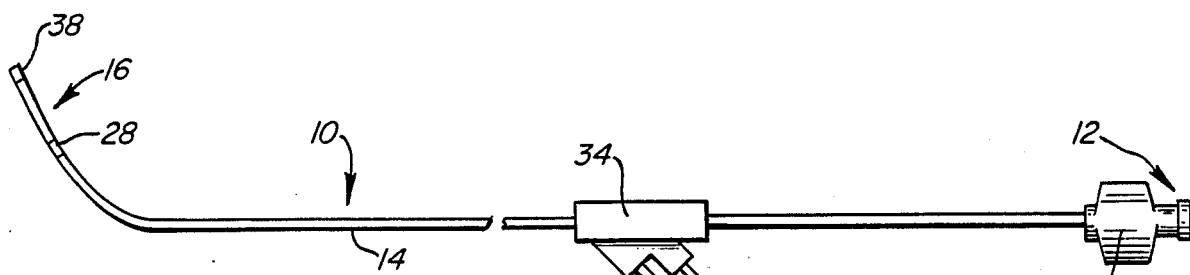
FIG. 1 is a plan view of a mapping, suction ablation catheter in accordance with this invention.

Referring to FIG. 1, a mapping suction ablation catheter 10 in accordance with this invention defines a proximal end 12, body 14, and distal end 16.

Body 14 may be conventionally made of an extruded polyurethane tube, over which stainless steel wire is braided, and having polyurethane extruded over the wire braid. Such wire braid is not shown in the sectional views of FIGS. 3 or 4 because it generally does not extend to distal end 16. The curved tip of catheter 10 may be preformed during fabrication. Generally, the construction of catheter 10 may be similar to the structure described in U.S. Pat. No. 3,485,234, except as otherwise described herein.

Central bore or lumen 18 is provided in each of the catheter embodiments. Additionally, within wall 20 of the catheter, two additional lumens, 22, 24, are provided as conduits, being electrically insulated by polyurethane material from the stainless steel braid.

Hub connector 26 may be of conventional design, being solvent bonded or the like to catheter body 14. The hub connector may be connected to either suction equipment for applying suction through the catheter, or to an infusion set for solutions, as may desired. Hub connector 26 may contain conventional features such as a stopcock control, and also an automatic anticoagulant drip mechanism, if desired.

A pair of electrodes 28, 30 are positioned in spaced relation at distal end portion 16 of catheter 10. Ring electrode 28 may be positioned on the order of 1.5 centimeters from the actual distal end 51 of catheter 10. Conductive lead wire 32 may be bonded to ring electrode 28, with lead wire 32 extending along the length of catheter 10 through lumen 22. Lead wire 32 extends along the catheter to and through central connector 34, to depart the catheter body in branching relation thereto as shown in FIG. 1, terminating in terminal pin 36. Lead wire 32 is preferably insulated along its length, particularly in its outer branching section.

Tubular electrode 30 is connected with lead wire 52 which extends through lumen 24 to central connector 34 and, in a manner similar to lead wire 32, branches outwardly from catheter body 14 at that point, to terminate in a terminal pin 54. As before, it is preferred to provide insulation to at least that portion of lead wire 52 which is outwardly branching.

Tubular electrode 30 is shown to be recessed within a tubular, ceramic insulating member 38, which may be made of molded alumina. The end surface 40 of the polyurethane catheter casing may be roughened, and adhesive used to adhere tubular, insulating member 38 to the catheter body 14. Typically, the outer diameter of insulating member 38 may be substantially equal to the outer diameter of the catheter body.

Electrode 30 defines a lesser diameter portion 44 which is contained within lumen 18 of catheter body 14 in an interference fit of conventional nature. To strengthen the interference fit, annular beads 46 may be provided on section 44 of electrode 30. Catheter body 14 may be heat sealed to section 44 of electrode 30, for example as the polyurethane is being cured during manufacture of the catheter.

Electrode 30 may be fabricated of a high temperature resistant alloy of tungsten and rhenium so as to be resistant to temperatures on the order of 3000 degrees C. and above. One specific alloy which may be used contains not less than 80 weight percent of rhenium. One useful tungsten-rhenium alloy is manufactured by Ultramet of Pacoima, Calif., having a melting point of 3280 degrees C.

Figure 3:
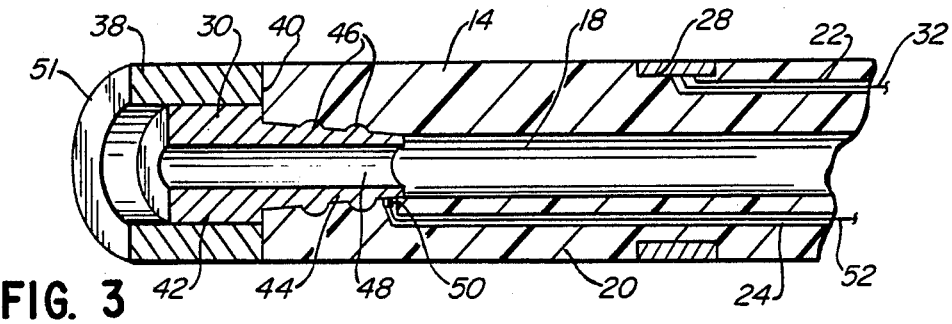
FIG. 3 is an enlarged, longitudinal sectional view taken along line 3—3 of FIG. 2.

Electrode 30 also defines central lumen 48 which communicates with lumen 18 of the catheter body, the distal section 42 of electrode 30 having a larger outer diameter than the inner section 44, as shown in FIG. 3. The walls of distal section 42 may typically have a thickness on the order of 0.015 to 0.02 inch.

Tab 50, made preferably of stainless steel, may be bonded by welding, soldering, or brazing onto stem portion 44 of electrode 30. Insulated copper lead wire 52 is then welded to tab 50 to provide electrical connection to the electrode.

The catheter of this invention may be used, as stated above, to destroy or inactivate tissue portions, specifically in the heart, but also any other tissue portion desired. For example, the catheter can be used to destroy small tumors, or to cauterize small tissue areas. A small tissue portion may be sucked into the distal end 51 of insulating member 38, as electrode 30 is energized with a strong pulse of direct current or RF cautery current, to create a pulse of tissue-destroying or inactivating energy which is localized by the presence of insulating member 38.

Figure 4:
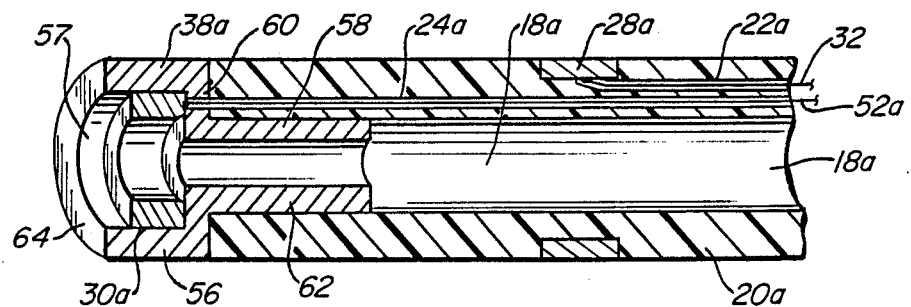
FIG. 4 is a longitudinal sectional view similar to FIG. 3 of an alternative embodiment of the catheter of this invention.

Turning now to FIG. 4, an alternative embodiment for a catheter tip in accordance with this invention is disclosed.

Figure 2:
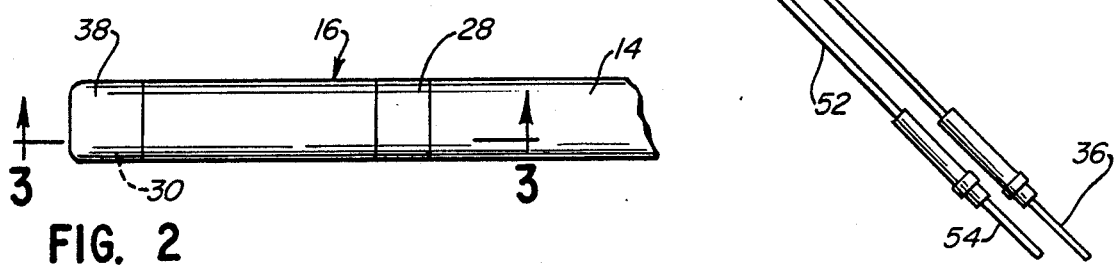
FIG. 2 is a magnified plan view of the distal end of the catheter of FIG. 1.

From the exterior, the catheter embodied in FIG. 4 may be essentially identical in appearance to the catheter of FIGS. 1–3. Catheter wall 20a, typically made of polyurethane, carries a ring electrode 28a, which is connected to lead 32a which extends through lumen 22a into a branching connection as in the previous embodiment. Central lumen 18a is defined in the catheter as before, communicating with a hub connector at the other end which may be identical to hub connector 26.

Tubular, refractory insulating member 38a is shown to be positioned at the distal end of the catheter, having a first section 58 of relatively small inner and outer diameter, which projects into lumen 18a of the catheter main body and is held therein by adhesion in a conventional manner and/or by frictional retention. Tubular insulating member 38a also has a second section 56 of larger inner and outer diameters than the corresponding respective inner and outer diameters of section 58.

Ring-shaped electrode 30a occupies bore 57 of the second tubular section 56, as shown.

Lead 52a extends through lumen 24a in a manner similar to the prior embodiment, passing through an aperture 60 in insulating member 38a to be secured at its end in electrical contact with electrode 30a. It can be seen that electrode 30a may be in recessed relation relative to the distal end 64 of insulating member 38a.

Accordingly, the catheter disclosed in FIG. 4 can be used in a manner similar to that of the previous embodiment. Suction pressure can be applied from the proximal end of the catheter through lumen 18a and bore 62 of insulating member 38a, to act on tissue surrounded by the distal end 64 of insulating member 38a. Ring electrode 30a may then be energized with a pulse of direct current or R.F. impulse to destroy or inactivate such tissue, while the effect of such electrical pulse or pulses may be localized by the shielding presence of insulating member 38a.

Insulating member 38a may be made of ceramic materials similar to insulating member 38 of the prior embodiment. Electrode 30a may be made of alloys similar to those previously described with respect to electrode 30.

Electrode 30a may have a wall thickness of about 0.015 to 0.020 inches, if desired. Electrode 30 may have an inner diameter of about 0.062 inch.

In the use of either of the embodiments of this invention, the endocardial wall of the heart, for example, may be mapped, using catheter 10 as a bipolar lead. In this circumstance, recessed electrode 30 or 30a may be used as one electrode, with the proximal ring electrode serving as the reference electrode. If, for example, one needs to destroy an atrioventricular node in order to eliminate the tachycardia symptoms, one may stabilize the catheter when the presence of the recorded bipolar and unipolar tip His Bundle deflection is stable and not modulated by respiration. Then, unipolar pacing may be initiated. If the time interval from stimulus to P wave is approximately equal to the stimulus to R interval, and each interval is roughly one-half the P-R interval, then the catheter tip may be located very close to the junction of the AV node to the His bundle. Suction may then be initiated to further stabilize the catheter, following which a direct current shock having an energy of 20 Joules, for example, is given to partially or completely destroy the atrioventricular node and to initiate heart block. In somewhat similar fashion, the physician can map the endocardial surface of the ventricle to obtain the site of the ectopic focus or reentry path, following which the catheter is stabilized, typically making use of the suction capability, and a D.C. or other shock is administered to deactivate the malfunctioning tissue.

The above has been offered for illustrative purposes only, and is not intended to limit the scope of the invention of this application, which is as defined in the claims below.

That which is claimed is:

1. In a catheter which comprises a tubular body having a bore, having an open distal end, and having a proximal aperture for applying suction through said catheter bore to the distal end, said catheter also having an electrode coupled to said tubular body adjacent said distal end and an electrode lead extending along said catheter for communication of the electrode with a power source, said electrode being adapted to contact body fluids and to provide electrical pulses when said catheter is placed within a living body, the improvement comprising, in combination:

a tubular refractory insulating member having a bore and positioned adjacent said distal end, said electrode being positioned within said insulating member, to localize the effects of electrical pulses emitted from said electrode.

2. The catheter of claim 1 in which said electrode is of tubular shape, fitting inside the bore of said tubular insulating member.

3. The catheter of claim 1 in which said refractory, insulating member is made of a ceramic to withstand and insulate against momentarily high catheter electrode temperatures.

4. The catheter of claim 1 in which said electrode is made of an alloy which does not significantly degrade at a temperature of at least 2000 degrees C.

5. The catheter of claim 4 in which said electrode consists essentially of an alloy of tungsten, rhenium, or both.

6. The catheter of claim 1 in which said tubular insulating member comprises a first section of relatively small inner and outer diameters, said catheter defining a tubular main body into which said first section projects and is secured, said insulating member also comprising a second section of larger inner and outer diameters which defines said distal end and which carries said electrode.

7. The catheter of claim 1 in which said electrode is tubular, said catheter defining a tubular main body into which said electrode projects and is secured, a portion of said electrode also projecting out of said main body, said insulating member surrounding said electrode portion and secured thereto.

8. The catheter of claim 1 in which said electrode is connected to a voltage source of any frequency from 0 to 1 GHz through said lead, to be used to inactivate malfunctioning tissue in the heart.

9. In a catheter which comprises a tubular body having a bore, having an open, distal end, and having a proximal aperture for applying suction through said catheter bore to the distal end, said catheter also having an electrode coupled to said tubular body adjacent said distal end, and an electrode lead extending along said catheter for communication of the electrode with a power source, said electrode being adapted to contact body fluids and to provide electrical pulses when said catheter is placed within a living body, the improvement comprising, in combination:

a tubular insulating member having a bore and made of a ceramic to withstand and insulate against momentarily high catheter electrode temperatures, said insulating member being positioned adjacent said distal end, said electrode being positioned within said insulating member to localize the effects of electrical pulses emitted from said electrode, said electrode being made of an alloy which does not significantly degrade at a temperature of at least 2000 degrees C.

10. The catheter of claim 9 in which said electrode is of tubular shape, fitting inside the bore of said tubular insulating member.

11. The catheter of claim 10 in which said tubular insulating member comprises a first section of relatively small inner and outer diameters, said catheter defining a tubular main body into which said first section projects and is secured, said insulating member also comprising a second section of larger inner and outer diameters which defines said distal end and which carries said electrode.

12. The catheter of claim 10 in which said catheter defines a tubular main body into which said electrode projects and is secured, a portion of said electrode also projecting out of said main body, said insulating member surrounding said electrode portion and secured thereto.

13. The catheter of claim 10 in which said electrode consists essentially of an alloy of tungsten, rhenium, or both.

14. The catheter of claim 10 in which said electrode is connected to a direct current source or a source of RF alternating current through said lead, to be used to inactivate malfunctioning tissue in the heart.

15. The catheter of claim 10 which further includes a second, ring shaped electrode carried on said tubular body in a position spaced from said other electrode and defining a second lead extending along said catheter for communication with electronic means for activating said electrode.

16. The catheter of claim 15 in which the leads of said electrodes diverge in separate, insulated, branching manner from the tubular body of said catheter at a position between the ends of said catheter.

* * * * *